United States Patent
Diaz et al.

(10) Patent No.: US 7,115,144 B2
(45) Date of Patent: *Oct. 3, 2006

(54) SPINAL IMPLANT

(75) Inventors: Robert L. Diaz, Palm Beach Gardens, FL (US); Robert L. Doubler, Ida, MI (US)

(73) Assignee: Joint Synergy, LLC, Palm Beach Gardens, FL (US)

( * ) Notice: Subject to any disclaimer, the term of this patent is extended or adjusted under 35 U.S.C. 154(b) by 262 days.

This patent is subject to a terminal disclaimer.

(21) Appl. No.: 10/792,399

(22) Filed: Mar. 2, 2004

(65) Prior Publication Data

US 2005/0197704 A1    Sep. 8, 2005

(51) Int. Cl.
*A61F 2/44* (2006.01)
(52) U.S. Cl. .................................................. 623/17.14
(58) Field of Classification Search ... 623/17.11–17.16
See application file for complete search history.

(56) References Cited

U.S. PATENT DOCUMENTS

| | | |
|---|---|---|
| 566,360 A | 8/1896 | White |
| 1,436,573 A | 11/1922 | Choppinet et al. |
| 2,836,442 A | 5/1958 | Moskovitz |
| 3,325,197 A | 6/1967 | Wehner |
| 3,426,364 A | 2/1969 | Lumb |
| 3,857,642 A | 12/1974 | Miller |
| 3,875,595 A | 4/1975 | Froning |
| 4,074,542 A | 2/1978 | Hankosky et al. |
| 4,156,070 A | 5/1979 | Jackson, Jr. et al. |
| 4,238,600 A | 12/1980 | Jackson, Jr. et al. |
| 4,257,129 A | 3/1981 | Volz |
| 4,289,123 A | 9/1981 | Dunn |
| 4,309,777 A | 1/1982 | Patil |
| 4,349,921 A | 9/1982 | Kuntz |
| 4,401,112 A | 8/1983 | Rezaian |
| 4,412,058 A | 10/1983 | Siemionko |
| 4,499,259 A | 2/1985 | Irwin |
| 4,605,417 A | 8/1986 | Fleischauer |
| 4,614,789 A | 9/1986 | Dicke et al. |
| 4,636,217 A | 1/1987 | Ogilvie et al. |
| 4,655,778 A | 4/1987 | Koeneman |
| 4,664,972 A | 5/1987 | Connolly |
| RE32,449 E | 6/1987 | Claussen et al. |
| 4,714,469 A | 12/1987 | Kenna |
| 4,749,769 A | 6/1988 | Kock et al. |
| 4,756,711 A | 7/1988 | Mai et al. |
| 4,759,766 A | 7/1988 | Buettner-Janz et al. |
| 4,759,769 A | 7/1988 | Hedman et al. |
| 4,770,659 A | 9/1988 | Kendall |
| 4,787,908 A | 11/1988 | Wyss et al. |

(Continued)

*Primary Examiner*—Corrine McDermott
*Assistant Examiner*—D. Jacob Davis
(74) *Attorney, Agent, or Firm*—McHale & Slavin, P.A.

(57) ABSTRACT

A spinal implant is inserted between adjacent vertebrae to function as an disk prosthesis. The prosthesis has two plates fastened to adjacent vertebrae facing each other. The facing sides of the plates each have a depending skirt formed as concentric arcs of about 90 degrees. The skirts are either bowed or tapered in the axial direction. A protrusion is centrally located between the arcs on one plate and a depression is centrally located between the arcs of the other plate. The plates are oriented to each other with the concentric arcs of each interrupted skirt at 90 degrees and the protrusion is engaged in the depression. The plates are then rotated about 90 degrees and the opposed arcs of one plate interlock with the opposed arcs of the other plate to prevent separation in the axial direction.

14 Claims, 3 Drawing Sheets

U.S. PATENT DOCUMENTS

| | | |
|---|---|---|
| 4,863,476 A | 9/1989 | Shepperd |
| 4,863,477 A | 9/1989 | Monson |
| 4,874,389 A | 10/1989 | Downey |
| 4,892,545 A | 1/1990 | Day et al. |
| 4,904,261 A | 2/1990 | Dove et al. |
| 4,919,666 A | 4/1990 | Buchhorn et al. |
| 4,932,969 A | 6/1990 | Frey et al. |
| 4,932,975 A | 6/1990 | Main et al. |
| 4,936,848 A | 6/1990 | Bagby |
| 4,946,378 A | 8/1990 | Hirayama et al. |
| 4,946,458 A | 8/1990 | Harms et al. |
| 4,955,908 A | 9/1990 | Frey et al. |
| 4,955,916 A | 9/1990 | Carignan et al. |
| 4,997,432 A | 3/1991 | Keller |
| 5,002,576 A | 3/1991 | Fuhrmann et al. |
| 5,024,670 A | 6/1991 | Smith et al. |
| 5,041,139 A | 8/1991 | Branemark |
| 5,047,055 A | 9/1991 | Bao et al. |
| 5,071,437 A | 12/1991 | Steffee |
| 5,123,926 A | 6/1992 | Pisharodi |
| 5,145,134 A | 9/1992 | Hashimoto et al. |
| 5,192,326 A | 3/1993 | Bao et al. |
| 5,236,460 A | 8/1993 | Barber |
| 5,246,458 A | 9/1993 | Graham |
| 5,258,031 A | 11/1993 | Salib et al. |
| 5,258,043 A | 11/1993 | Stone |
| 5,306,307 A | 4/1994 | Senter et al. |
| 5,306,308 A | 4/1994 | Gross et al. |
| 5,306,309 A | 4/1994 | Wagner et al. |
| 5,308,412 A | 5/1994 | Shetty et al. |
| 5,314,477 A | 5/1994 | Marnay |
| 5,320,644 A | 6/1994 | Baumgartner |
| 5,360,430 A | 11/1994 | Lin |
| 5,370,697 A | 12/1994 | Baumgartner |
| 5,401,269 A | 3/1995 | Buttner-Janz et al. |
| 5,404,182 A | 4/1995 | Nomura |
| 5,414,704 A | 5/1995 | Spinney |
| 5,425,773 A | 6/1995 | Boyd et al. |
| 5,425,777 A | 6/1995 | Sarkisian et al. |
| 5,458,638 A | 10/1995 | Kuslich et al. |
| 5,458,641 A | 10/1995 | Ramirez Jimenez |
| 5,458,642 A | 10/1995 | Beer et al. |
| 5,474,555 A | 12/1995 | Puno et al. |
| 5,489,308 A | 2/1996 | Kuslich et al. |
| 5,507,816 A | 4/1996 | Bullivant |
| 5,534,029 A | 7/1996 | Shima |
| 5,534,030 A | 7/1996 | Navarro et al. |
| 5,538,427 A | 7/1996 | Hoffman et al. |
| 5,549,680 A | 8/1996 | Gordon |
| 5,556,431 A | 9/1996 | Buttner-Janz |
| 5,562,738 A | 10/1996 | Boyd et al. |
| 5,566,687 A | 10/1996 | Trapanovski |
| 5,588,625 A | 12/1996 | Beak |
| 5,603,478 A | 2/1997 | Wang |
| 5,645,596 A | 7/1997 | Kim et al. |
| 5,674,296 A | 10/1997 | Bryan et al. |
| 5,676,701 A | 10/1997 | Yuan et al. |
| 5,683,465 A | 11/1997 | Shinn et al. |
| 5,782,832 A | 7/1998 | Larsen et al. |
| 5,893,889 A | 4/1999 | Harrington |
| 5,895,428 A | 4/1999 | Berry |
| 5,899,941 A | 5/1999 | Nishijima et al. |
| 6,001,130 A | 12/1999 | Bryan et al. |
| 6,019,792 A | 2/2000 | Cauthen |
| 6,039,763 A | 3/2000 | Shelokov |
| 6,063,121 A | 5/2000 | Xavier et al. |
| 6,146,421 A | 11/2000 | Gordon et al. |
| 6,179,874 B1 | 1/2001 | Cauthen |
| 6,228,118 B1 | 5/2001 | Gordon |
| 6,416,551 B1 | 7/2002 | Keller |
| 6,517,580 B1 | 2/2003 | Ramadan et al. |
| 6,579,321 B1 | 6/2003 | Gordon et al. |
| 6,682,562 B1 | 1/2004 | Viart et al. |
| 2004/0193273 A1* | 9/2004 | Huang .................... 623/17.12 |

* cited by examiner

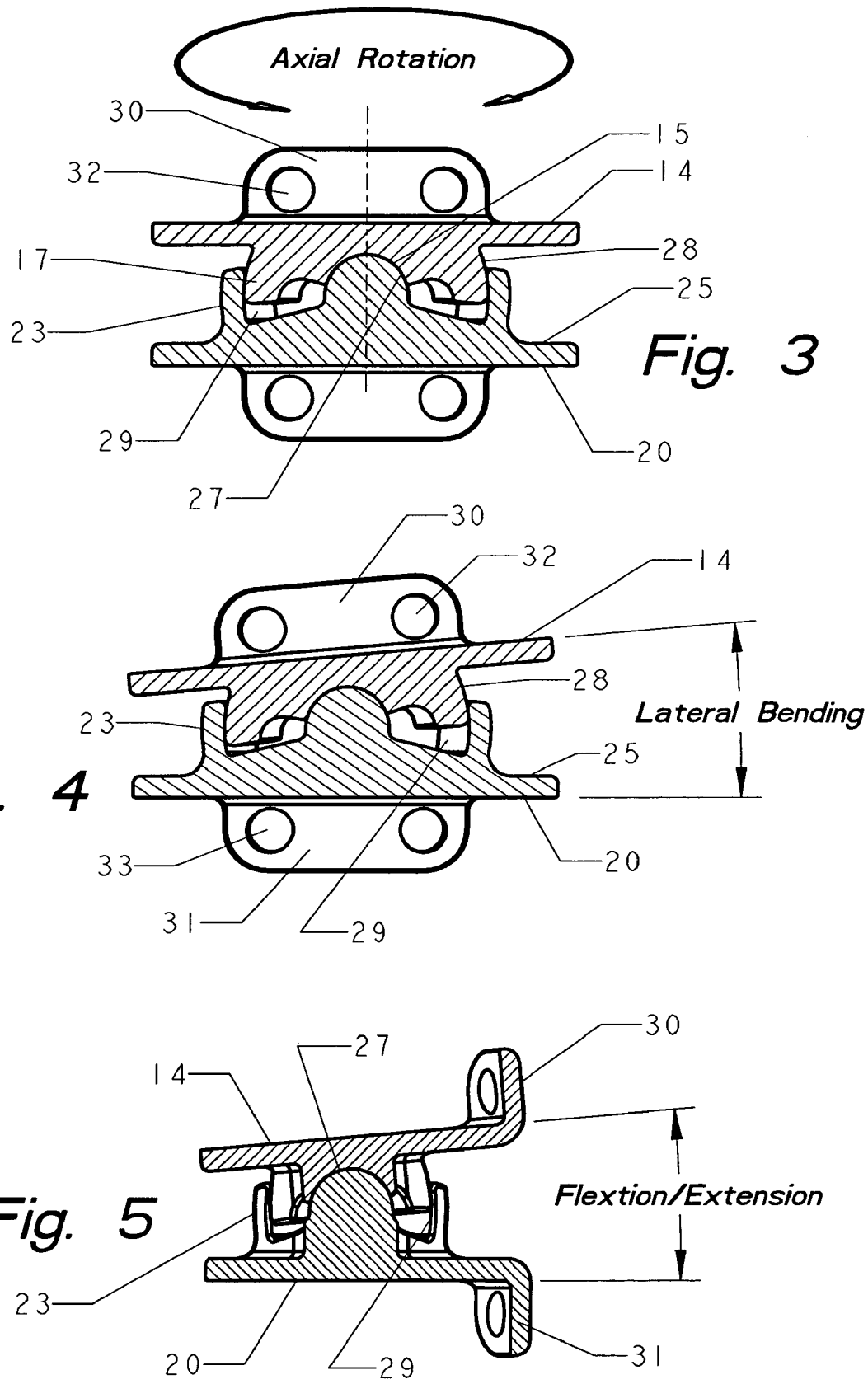

SPINAL IMPLANT

FIELD OF THE INVENTION

This invention relates to orthopedic surgery and, in particular, spinal implants for replacement of ruptured or excised spinal disks.

BACKGROUND OF THE INVENTION

Several attempts have been made to design a spinal prosthesis for replacement of missing or excised disk material that replicates the functions of the missing tissue. U.S. Pat. No. 4,759,769 to Hedman et al discloses a two piece artificial disk device in which two plates are attached to the adjacent vertebrae by bone screws inserted through flanges on the plates. A spring biasing mechanism is captured between the plates to simulate the actions of the natural disk material. U.S. Pat. No. 5,246,458 to Graham and U.S. Pat. No. 6,228,118 to Gordon disclose other intervertebral implants with arcuate flanges used to connect the device to adjacent vertebra.

The patents to Marnay, U.S. Pat. No. 5,314,477, Buttner-Janz et al, U.S. Pat. No. 5,401,269, Yuan et al, U.S. Pat. No. 5,676,701, and Shelokov, U.S. Pat. No. 6,039,763, all are directed to the design of the opposing faces of the adjacent plates of an implant to provide a limited universal joint to simulate the natural movement of the spine.

U.S. Pat. No. 5,683,465 to Shinn et al teaches two plates with bow shaped skirts which are interlocked.

What is needed in the art is a disk prosthesis that has limited universal motion yet is securely interlocked to prevent dislocation or separation.

SUMMARY OF THE PRESENT INVENTION

A spinal implant for insertion between adjacent vertebrae to function as an disk prosthesis. The prosthesis is formed from two plates fastened to adjacent vertebrae facing each other. The facing sides of the plates each have a depending skirt formed as concentric arcs of about 90 degrees. The skirts are either bowed or tapered in the axial direction. A protrusion is centrally located between the arcs on one plate and a depression is centrally located between the arcs of the other plate. The plates are oriented to each other with the concentric arcs of each interrupted skirt at 90 degrees and the protrusion is engaged in the depression. The plates are then rotated about 90 degrees and the opposed arcs of one plate interlock with the opposed arcs of the other plate to prevent separation in the axial direction.

Therefore, it is an objective of this invention to provide a spinal implant for axial support of the spinal column which replicates the dimensions and function of an intervertebral disk.

It is another objective of this invention to provide a kit including all the components for assembly and surgical placement of an artificial spinal disk.

It is a further objective of this invention to provide a method of assembly of the components of the kit which results in an axially interlocked spinal implant.

It is yet another objective of this invention to provide a modified ball and socket joint between two plates attached to adjacent vertebrae permitting lateral rotation, lateral bending and vertical tilting.

It is a still further objective of this invention to provide shaped interrupted skirts on two plates which act as stop limits for tilting and bending.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

SHORT DESCRIPTION OF THE DRAWINGS

FIG. 3 is a frontal view, partially in section, of the assembled implant of this invention showing axial rotation;

FIG. 4 is a frontal view, partially in section, of the assembled implant showing a positive bend;

FIG. 5 is a side view, partially in section, of the assembled implant showing flexion/extension;

DETAILED DESCRIPTION OF THE INVENTION

Figure 1:
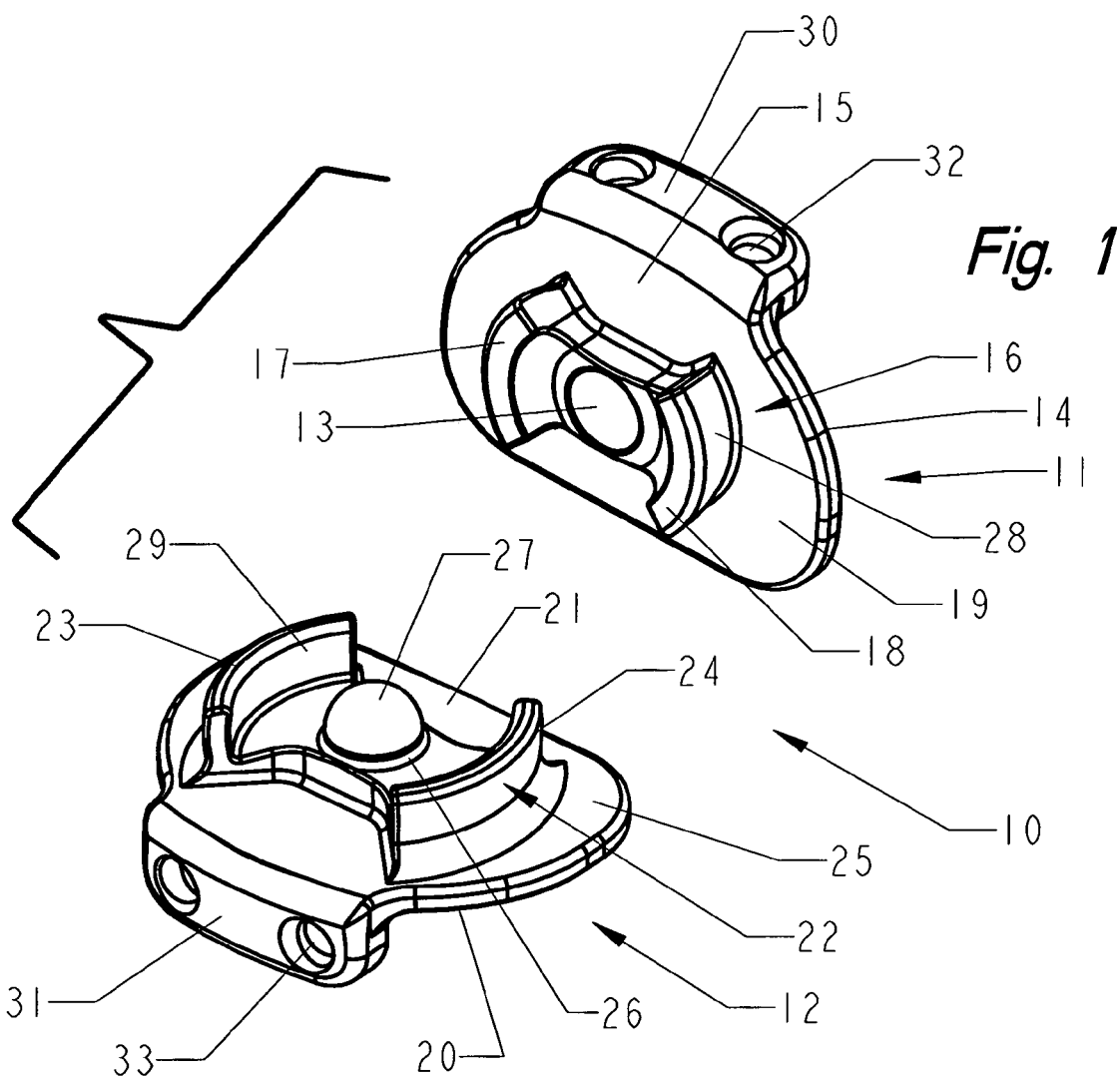
FIG. 1 is a perspective of the disassembled kit of this invention.

The spinal implant 10, shown in FIG. 1, has two major components, an upper plate 11 and a lower plate 12. For purposes of illustration only, the upper plate 11 is shown with a dome shaped depression 13. Of course, the position of the plates can be reversed, in use. Both upper plate 11 and lower plate 12 have a plan form substantially the size and shape of the end wall of the vertebra between which the implant will be placed to produce the maximum area of contact between the implant and the vertebra for stability and support. Obviously, different sized plates are necessary because of the difference in size of vertebra within a spinal column and the different sizes or ages of patients.

The upper plate 11 has a planar surface 14 for contact with the end wall of a vertebra and an opposite disk surface 15. Depending from the disk surface is an interrupted skirt 16 with opposed arcs 17 and 18. The arcs are approximately 180 degrees apart at their centers and extend about 90 degrees. The diameter of the arcs is less than the periphery of the plate 11 leaving a horizontal flange 19. Centrally located within the semi-circular arcs is the dome shaped depression or concavity 13.

The lower plate 12 has a planar surface 20 for contact with the end wall of a vertebra and an opposite disk surface 21. Upstanding from the disk surface is an interrupted skirt 22 with opposed arcs 23 and 24. The arcs are approximately 180 degrees apart at their centers and extend about 90 degrees. The diameter of the arcs is less than the periphery of the plate 12 leaving a horizontal flange 25. Centrally located within the semi-circular arcs is the protrusion 26. The end 27 of the protrusion is rounded and shaped to closely fit the contours of the depression 13. The protrusion 26 is of such dimensions as to support the weight of the spinal column.

As shown, though the relationship could be reversed, the opposed arcs 17 and 18 of the depending interrupted skirt 16 are concentric with the opposed arcs 23 and 24 of the upstanding interrupted skirt and of lesser diameter allowing rotation of the plates relative to each other with surface contact between the outer surface 28 of the depending arcs and the inner surface 29 of the upstanding arcs.

Figure 2:
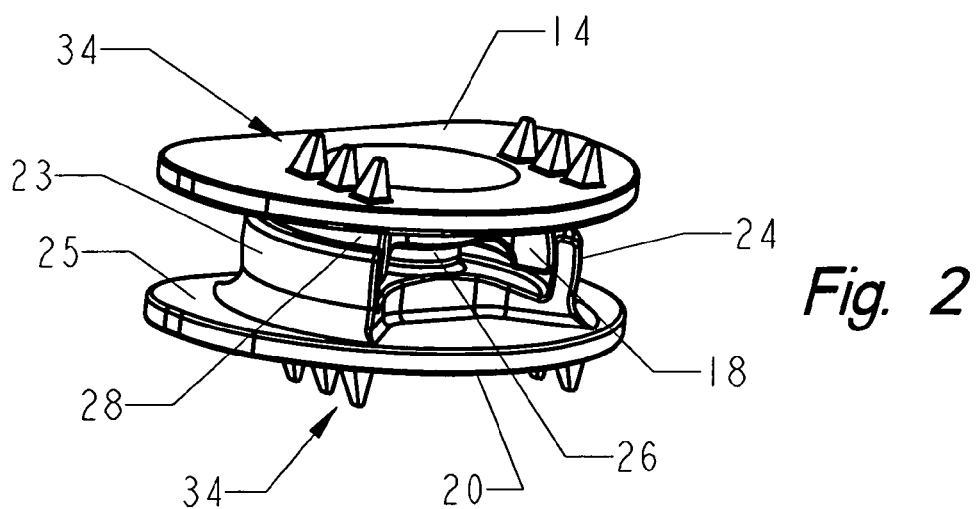
FIG. 2 is a perspective of the assembled spinal implant of this invention with alternative fasteners.

As shown in FIG. 1, each of plates of the spinal implant has fastener flanges 30 and 31 approximately normal to the vertebra contacting surfaces 14 and 20. The flanges have apertures 32, 33 which cooperate with bone screws to mount the spinal implant on the vertebra. The fastener flanges 30, 31 may be on the anterior surface or posterior of the vertebra. Also, in FIG. 2, an alternative fastener is shown in the form of spikes 34 which are driven into the end walls of the adjacent vertebra. Of course, the two fasteners may be used together.

The spinal implant provides support and range of motion similar to the natural joint in that the plates 11 and 12 may rotate axially, as shown in FIG. 3, limited by natural anatomical structures. The spine may bend laterally, as shown in FIG. 4, and tilt medially in flexion/extension, as shown in FIG. 5, in a range of approximately + or −10 degrees from center. The implant also provides limitation of these movements through interaction of the depending arcs and the upstanding arcs.

Figure 6:
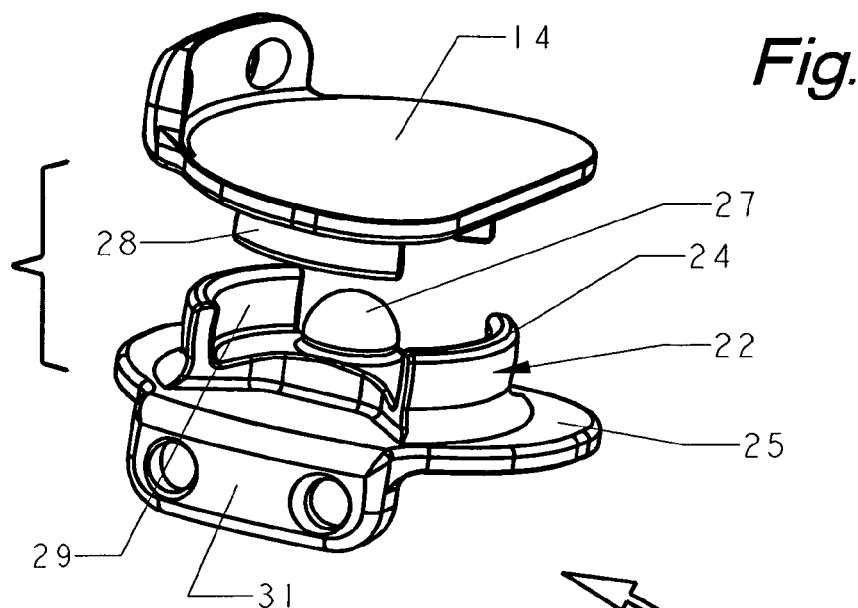
FIG. 6 is a perspective of the assembly position of the kit of this invention.
Figure 7:
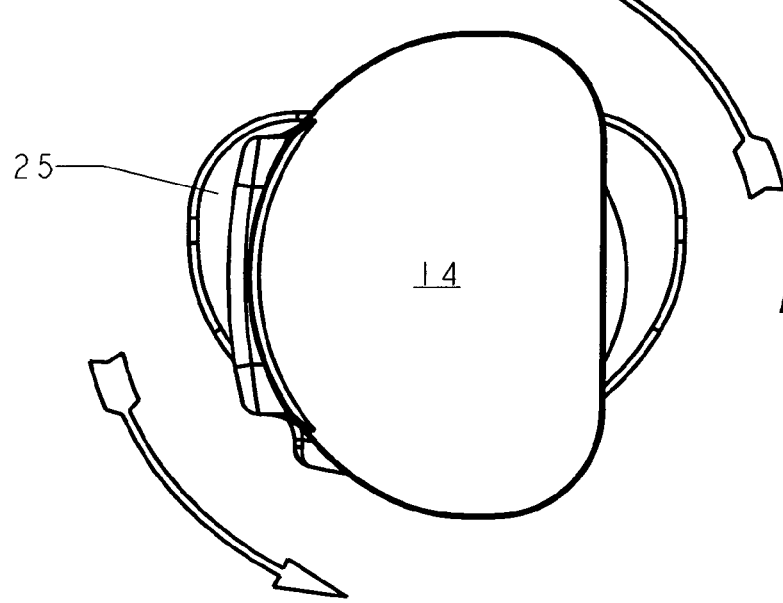
FIG. 7 is a top plan view of the implant showing the relative rotation for assembly.

As shown in FIG. 6, the components of the kit are connected together by orienting the interrupted skirts 16 and 22 at 90 degrees to each other then placing the rounded end 27 of the protrusion 26 in the concavity 13. This action overlaps the interrupted skirts vertically. The plates are rotated through 90 degrees relative to each other, as shown in FIG. 7. This rotation aligns the depending opposed arcs with the upstanding opposed arcs and interlocks the plates in a movable joint that cannot be separated axially. The outer surface 28 of the interrupted skirt 16 slidably contacts the inner surface 29 of the interrupted skirt 22. The contacting surfaces are spherical or bowed, as shown in FIGS. 3 and 4, forming another ball and socket joint with the bottom edge of the depending arc 23 of a larger diameter than the top edge of the upstanding arc 17 by which the plates are interlocked. The components are made from materials that are suitable for implantation in the living body and have the requisite strength to perform the described functions without deformation, e.g., surgical stainless steel, titanium, and alloys of each, coated metals, ceramics, ceramic coatings, and polymer coatings. The surfaces may be coated or otherwise treated to promote bone in-growth. In the high wear areas, such as the rounded end of the protrusion and the depression, coatings or inserts may be used to prevent galling and permit repair.

Figure 8:
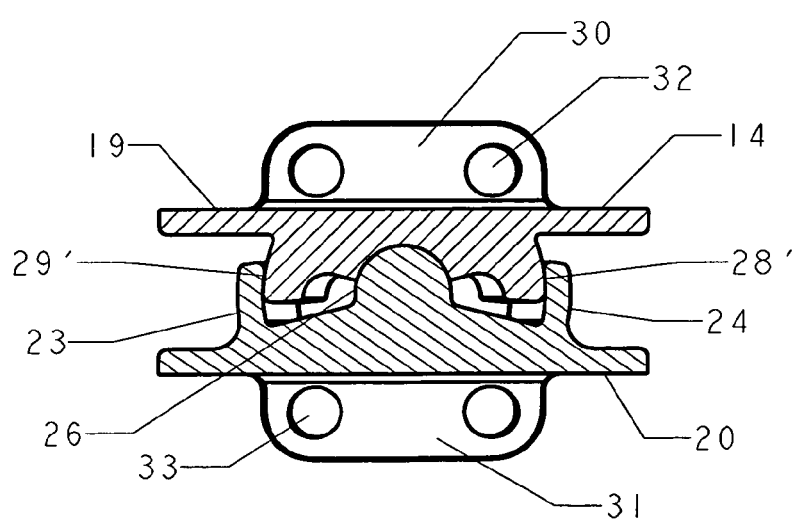
FIG. 8 is a frontal view, partially in section, of a modification of the assembled implant.

FIG. 8 illustrates a modification of the spherical contacting surfaces of the interrupted skirts. In this embodiment, the contacting surfaces 28' and 29' of the interrupted skirts are straight and conical or tapered. The contacting surfaces of the upstanding and depending arcs are of slightly different diameters and formed as congruent angles with the disk surfaces of the plates.

The kit contains plates with protrusions and skirts of varying lengths to allow selection of components for an implant with the axial dimension substantially the same as the thickness of the disk the implant will replace. The kit may also contain upper and lower plate components of varying sizes.

A number of embodiments of the present invention have been described. Nevertheless, it will be understood that various modifications may be made without departing from the spirit and scope of the invention. Accordingly, it is to be understood that the invention is not to be limited by the specific illustrated embodiment but only by the scope of the appended claims.

We claim:

1. A spinal prosthesis kit for placement between adjacent vertebrae to replace disk material comprising a first plate and a second plate, said first plate having a planar vertebrae engaging side and a disk side, a first interrupted skirt on said disk side extending approximately normal to said first plate, said skirt formed as opposing arcs, a depression in said disk side of said first plate centrally located between said opposing arcs, said second plate having a second planar vertebrae engaging side and a second disk side, a second interrupted skirt on said second disk side extending approximately normal to said second plate, said second skirt formed as opposing arcs, a protrusion on said second disk side of said second plate centrally located between said opposing arcs whereby said first plate is adapted to contact a vertebrae and said second plate is adapted to contact an adjacent vertebrae with said depression forming a bearing surface for said protrusion that does not interlock therewith, whereby said first and second interrupted skirts interlock to prevent axial separation of said first and second plates forming a universal joint.

2. A spinal prosthesis kit for placement between adjacent vertebrae of claim 1 wherein said first interrupted skirt and said second interrupted skirt are concentric in a plane parallel with said first and second plates, said opposed arcs of said first interrupted skirt are adapted to contact said opposed arcs of said second interrupted skirt.

3. A spinal prosthesis kit for placement between adjacent vertebrae of claim 2 wherein said opposed arcs of said first interrupted skirt and said second interrupted skirt extend approximately 90 degrees relative to each of said first interrupted skirt and said second interrupted skirt, respectively.

4. A spinal prosthesis kit for placement between adjacent vertebrae of claim 2 wherein said opposed arcs of said first interrupted skirt and said opposed arcs of said second interrupted skirt are concentric segments of a circle in a plane parallel to said first and second plates whereby said concentric segments of said first interrupted skirt are adapted to contact said concentric segments of said second interrupted skirt to form an interlocked universal joint.

5. A spinal prosthesis kit for placement between adjacent vertebrae of claim 1 wherein said opposed arcs of said first interrupted skirt and said opposed arcs of said second interrupted skirt are concentric segments of a circle in a plane parallel to said first and second plates whereby said concentric segments of said first interrupted skirt are adapted to contact said concentric segments of said second interrupted skirt to form an interlocked universal joint.

6. A spinal prosthesis kit for placement between adjacent vertebrae of claim 5 wherein said first plate and said second plate each includes a fastener on said disk side adapted to fix said plate to the respective vertebrae.

7. A spinal prosthesis kit for placement between adjacent vertebrae of claim 6 wherein a first fastener on said first plate and a second fastener on said second plate each includes a first flange and a second flange extending approximately normal to said first vertebrae engaging side and said second vertebrae engaging side, respectively, at least one aperture through said first flange and said second flange for accepting a bone screw whereby said first plate and said second plate may be attached to adjacent vertebrae.

8. A spinal prosthesis kit for placement between adjacent vertebrae of claim 1 wherein said first plate includes a first fastener and said second plate includes a second fastener each said fastener having a first flange and a second flange extending approximately normal to said first vertebrae engaging side and said second vertebrae engaging side, respectively, at least one aperture through said first flange and said second flange for accepting a bone screw whereby said first plate and said second plate may be attached to adjacent vertebrae.

9. A spinal prosthesis kit for placement between adjacent vertebrae of claim 1 wherein said first interrupted skirt and said second interrupted skirt are tapered.

10. A spinal prosthesis for placement between adjacent vertebrae for axial support comprising a first plate and a second plate, said first plate having a planar vertebrae engaging side and a disk side, a first fastener on said planar side for engaging a vertebrae, a first interrupted skirt on said disk side extending approximately normal to said first plate, said first interrupted skirt formed as opposing arcs, a depression in said disk side of said first plate centrally located between said opposing arcs, said second plate having a second planar vertebrae engaging side and a second disk side, a second fastener on said second planar side for engaging a vertebrae, a second interrupted skirt on said second disk side extending approximately normal to said second plate, said second skirt formed as opposing arcs, a protrusion on said second disk side of said second plate centrally located between said opposing arcs, said protrusion inserted in said depression, said depression forming a bearing surface for said protrusion that does not interlock therewith, said first interrupted skirt and said second interrupted skirt being concentric in a plane parallel with said first and second plates, said opposed arcs of said first interrupted skirt contacting said opposed arcs of said second interrupted skirt, said opposed arcs of said first interrupted skirt and said opposed arcs of said second interrupted skirt being concentric segments of a circle in a plane parallel to said first and second plates whereby said concentric segments of said first interrupted skirt contact said concentric segments of said second interrupted skirt are interlocked to prevent axial separation forming a universal joint.

11. A spinal prosthesis for placement between adjacent vertebrae of claim 10 wherein said concentric segments are adapted to rotate approximately plus or minus 10 degrees relative to each other.

12. A method of assembly of a spinal prosthesis comprising the steps of:

a) providing a first plate, said first plate having a planar vertebrae engaging side and a disk side, a first interrupted skirt on said disk side extending approximately normal to said plate, said skirt formed as opposing arcs, a depression forming a bearing surface in said disk side of said plate centrally located between said opposing arcs;

b) providing a second plate having a second planar vertebrae engaging side and a second disk side, a second interrupted skirt on said second disk side extending approximately normal to said second plate, said second skirt formed as opposing arcs, a protrusion on said second disk side of said second plate centrally located between said opposing arcs;

c) orienting said first plate and said second plate parallel with each other with said interrupted skirt of said first plate located between said opposing arcs of said second plate;

d) moving said interrupted skirt of said first plate between said opposing arcs of said second plate and engaging said protrusion in said bearing surface of said depression in axial alignment, that does not interlock therewith; and e) rotating said first plate and said second plate about the axis relative to each other until said interrupted skirt of said first plate contacts said opposing arcs of said second plate whereby said interrupted skirt of said first plate and said interrupted skirt of said second plate are interlocked to prevent axial separation.

13. A method of assembly of a spinal prosthesis of claim 12 comprising the steps of:

a) pivoting said protrusion in said depression plus and minus approximately 10 degrees from the axis in the direction of said opposed arcs and b) said pivoting limited by said interrupted skirt of said first plate contacting said second plate.

14. A method of assembly of a spinal prosthesis of claim 12 comprising the steps of:

a) pivoting said protrusion in said depression plus and minus approximately 10 degrees from the axis in the direction away from said opposed arcs, and b) said pivoting limited by said interrupted skirt of said first plate contacting said interrupted skirt of said second plate.

* * * * *